US00PP22776P3

(12) United States Plant Patent
Danziger

(10) Patent No.: US PP22,776 P3
(45) Date of Patent: Jun. 5, 2012

(54) ***SALVIA* PLANT NAMED 'DANSALFN13'**

(50) Latin Name: *Salvia farinacea*
Varietal Denomination: DANSALFN13

(75) Inventor: Gavriel Danziger, Moshav Nir-Zvi (IL)

(73) Assignee: Danziger 'Dan' Flower Farm

( * ) Notice: Subject to any disclaimer, the term of this patent is extended or adjusted under 35 U.S.C. 154(b) by 0 days.

(21) Appl. No.: 12/805,426

(22) Filed: Jul. 30, 2010

(65) Prior Publication Data

US 2012/0030848 P1 Feb. 2, 2012

(51) Int. Cl.
*A01H 5/00* (2006.01)

(52) U.S. Cl. ..... Plt./475

(58) Field of Classification Search ..... Plt./475
See application file for complete search history.

(56) References Cited

OTHER PUBLICATIONS

Printout of application information from Community Plant Variety Office (CPVO) website for corresponding CPVO application No. 2010/1300 filed Jul. 2, 2010 (1 page) (http://www.cpvoextranet.cpvo.europa.eu).

*Primary Examiner* — June Hwu

(57) ABSTRACT

A new and distinct *Salvia farinacea* plant named 'DANSALFN13' particularly characterized by bilabiate-shaped flowers with petals in shades of white; upright and compact growth habit; freely branching and flowering plant habit; about 6 to 8 weeks flowering response and stays in full bloom in moderate climate; and good weather tolerance with a preferred temperature range of 5° C. to 35° C.

2 Drawing Sheets

Latin name of the genus and species of the plant claimed: *Salvia farinacea.*

Variety denomination: 'DANSALFN13'.

BACKGROUND OF THE INVENTION

The present invention relates to a new and distinct cultivar of *Salvia* plant, botanically known as *Salvia farinacea* of the Lamiaceae family, and hereinafter referred to by the variety denomination 'DANSALFN13'.

The new *Salvia farinacea* 'DANSALFN13' is a product of a planned breeding program conducted by the inventor, Gavriel Danziger, in Moshav Mishmar Hashiva, Israel. The objective of the breeding program was to develop a new *Salvia farinacea* cultivar with compact and well branched habit with white flower color.

The new *Salvia farinacea* 'DANSALFN13' originated in 2007 as a result of open pollination between two unknown, unpatented, *Salvia farinacea* plants growing in a field in the controlled breeding program conducted by the inventor, Gavriel Danziger, in Moshav Mishmar Hashiva, Israel (please confirm).

The new *Salvia farinacea* 'DANSALFN13' was discovered and selected by the inventor, Gavriel Danziger, as a single flowering plant within the progeny of the stated open pollination cross in a controlled environment in 2007 in Moshav Mishmar Hashiva, Israel.

Asexual reproduction of the new *Salvia farinacea* 'DANSALFN13' by vegetative cuttings was first performed in August of 2008 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'DANSALFN13' which in combination distinguish this *Salvia farinacea* as a new and distinct cultivar:

1. Plants produce bilabiate-shaped flowers with petals in shades of white;
2. Upright and compact growth habit;
3. Freely branching and flowering plant habit;
4. About 6 to 8 weeks flowering response and stays in full bloom in moderate climate; and
5. Good weather tolerance with a preferred temperature range of 5° C. to 35° C.

The new *Salvia farinacea* 'DANSALFN13' is an open pollination product and therefore, can not be compared to its parents.

Of the many commercial cultivars known to the present inventor, the most similar in comparison to the new *Salvia farinacea* 'DANSALFN13' is the *Salvia farinacea* 'DANSALFUN1' (patented, U.S. Plant Pat. No. 19,788), also know by the tradename of *Salvia* Sallyfun Blue. Plants of 'DANSALFN13' differ from plants of the 'DANSALFUN1' in the characteristics described in Table 1:

TABLE 1

| Trait | New Cultivar 'DANSALFN13" | Comparison Cultivar 'DANSALFUN1' (patented) |
|---|---|---|
| Mature Flower Color (upper surface) | Petal shades of white, closest to RHS N999D | Petal shades of violet-blue, closest to RHS 94A |
| Inflorescence size | Height: About 10 cm to 15 cm<br>Diameter: About 5 cm | Height: About 15 cm to 18 cm<br>Diameter: About 1.5 cm |

TABLE 1-continued

| Trait | New Cultivar 'DANSALFN13" | Comparison Cultivar 'DANSALFUN1' (patented) |
|---|---|---|
| Flower size (lower lip) | Depth: About 0.8 cm Width: About 1.0 cm | Depth: About 0.7 cm Width: About 1.0 cm |

BRIEF DESCRIPTION OF THE PHOTOGRAPHS

The accompanying photographs illustrate the overall appearance of the new *Salvia* 'DANSALFN13' showing the colors as true as is reasonably possible with colored reproductions of this type. Colors in the photographs may differ slightly from the color values cited in the detailed botanical description, which accurately describe the color of 'DANSALFN13'.

DETAILED BOTANICAL DESCRIPTION

Figure 1:
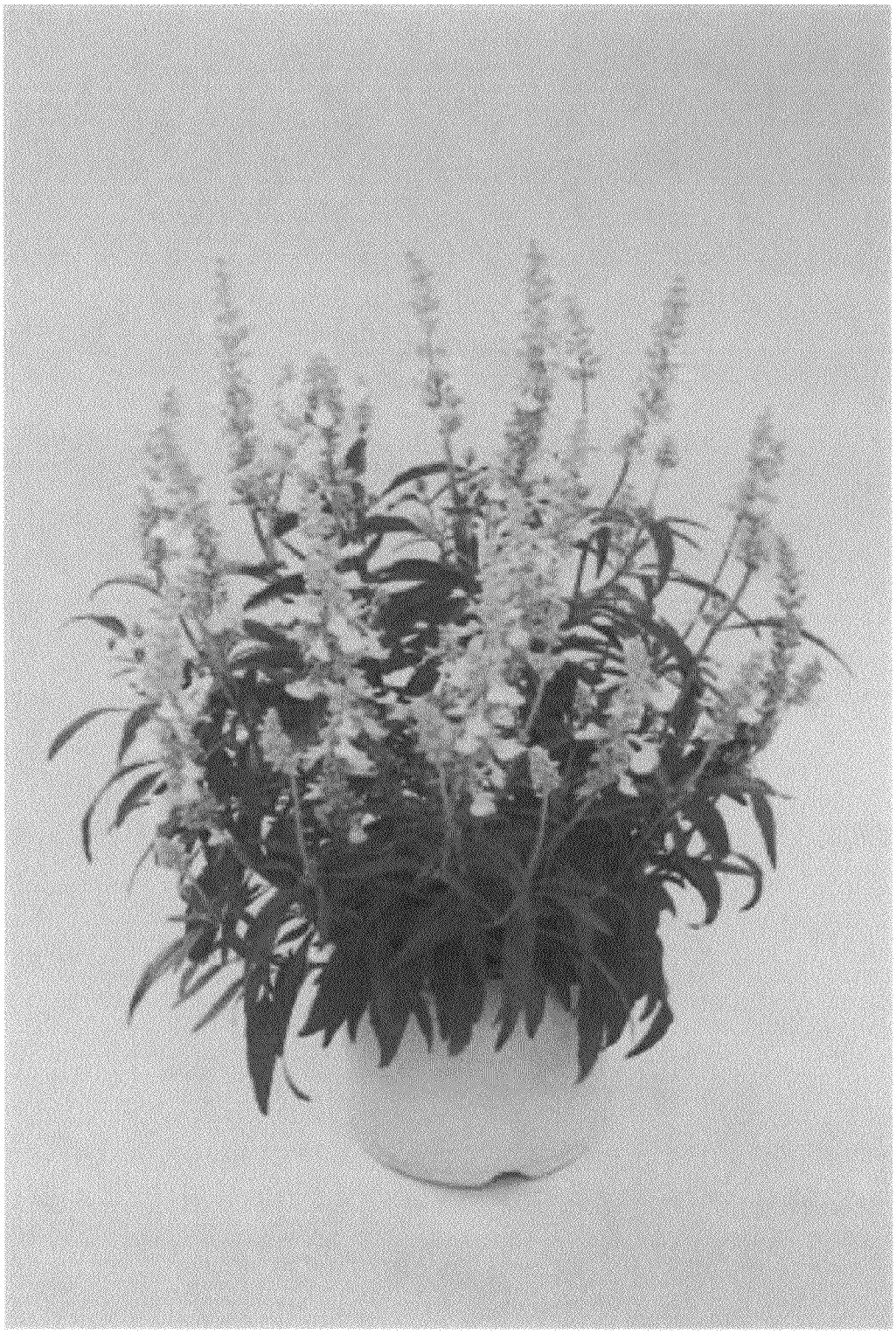
FIG. 1 shows a side perspective view of a typical flowering plant of 'DANSALFN13' in a 12 cm, potted at 2 months of age.
Figure 2:
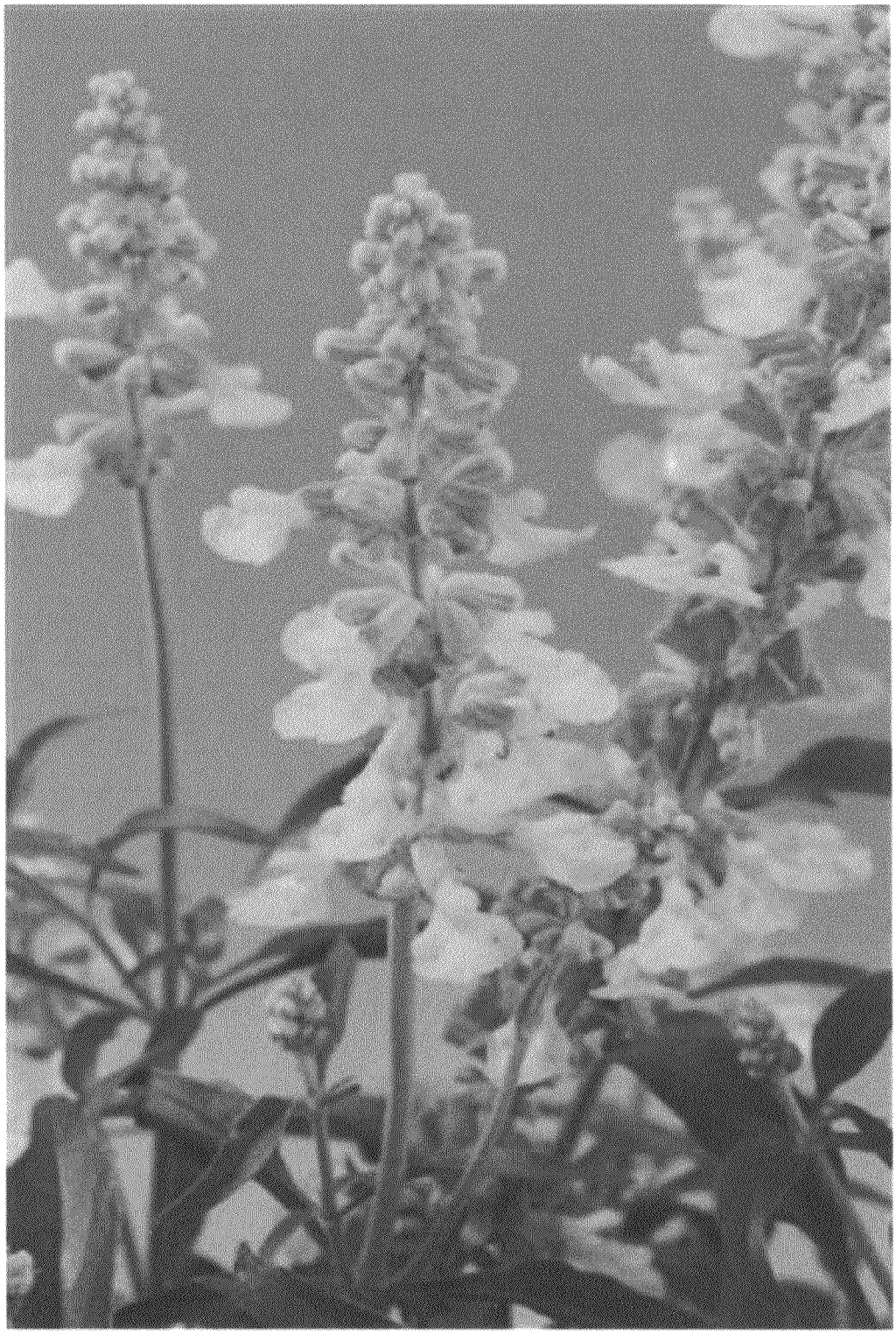
FIG. 2 shows a close-up of the typical flowers, buds and leaves of 'DANSALFN13', potted at 2 months of age.

The new *Salvia* 'DANSALFN13' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANSALFN13' as grown in a greenhouse in Moshav Mishmar Hashiva, Israel, under conditions which closely approximate those generally used in commercial practice. Optimal growth conditions include that plants of 'DANSALFN13' are grown outdoors in a moderate climate and indoors during the winter season. Irrigation and fertilization are recommended on a regular basis. Plants of 'DANSALFN13' are usually grown in full sunlight. Plants of 'DANSALFN13' are fully grown in 1½ months from planting a cutting in the summer season and bloom all year-round in a moderate climate. The 'DANSALFN13' plants described herein were grown indoors in 12 cm pots in a glass greenhouse in Moshav Mishmar Hashiva, Israel, with the day temperatures ranging from 18° C. to 28° C. and night temperatures ranging from 11° C. to 18° C. Plants of 'DANSALFN13' were fertilized up to a level of 250-300 ppm N. No growth retardant(s) are used.

Color references are made to The Royal Horticultural Society Colour Chart (R.H.S.), 2001 edition, except where general colors of ordinary significance are used. Color values were taken under daylight conditions at approximately noon in Moshav Mishmar Hashiva, Israel. The age of the 'DANSALFN13' plants described is 8 weeks.

Botanical: *Salvia farinacea.*

Parentage:

*Seed parent*.—Unknown, unpatented *Salvia farinacea* cultivar.

*Pollen parent*.—Open pollination.

Propagation:

*Type*.—Vegetative cuttings.

*Rooting habit and description*.—Fine, fibrous and freely branching.

*Time to initiate roots*.—About 5 to 8 days at 25° C.

*Time to produce a rooted cutting*.—About 21 days at 25° C.

Plant:

*Form*.—Upright and erect.

*Growth habit*.—Compact.

*Height (from soil level to top of plant)*.—About 30 cm to 40 cm.

*Spread*.—About 20 cm to 30 cm.

*Cold tolerance*.—Frost tender. Temperatures below 5° C. may damage plants.

*Vigor*.—Vigorous growth; plants are fully grown in 1.5 months from planting cutting in during summer season.

Lateral branch:

*Quantity per plant*.—About 35 to 40.

*Strength*.—Strong.

*Length*.—About 14 cm.

*Diameter*.—About 0.3 cm.

*Aspect*.—Upright.

*Texture*.—Glabrous with very delicate short feathers like hairs.

*Color*.—Yellow Green group, RHS 144A.

*Internode length*.—About 1.5 cm to 2 cm.

*Internode color*.—Yellow Green group, RHS 144A.

Foliage:

*Quantity of leaves per lateral branch*.—About 10 to 12.

*Type*.—Simple.

*Arrangement*.—Opposite.

*Length*.—About 6 cm.

*Width*.—About 2 cm.

*Overall shape of leaf*.—Lance-shaped.

*Apex*.—Acute.

*Base*.—Attenuate.

*Margin*.—Very delicate, serrate.

*Texture*.—Upper surface: Glabrous. Under surface: Slightly pubescent.

*Color of upper surface*.—Mature leaf: Green, RHS 137C. Immature leaf: Yellow-green, RHS 146B.

*Color of under surface*.—Mature leaf: Green, RHS 137B. Immature leaf: Yellow-green, RHS 146B.

*Fragrance*.—Very delicate, sage-like fragrance.

*Venation*.—Pattern: Pinnate. Color: Upper surface: Yellow-green, RHS147D. Under surface: Yellow-green, RHS 146C.

*Petioles*.—Length: About 0.6 cm to 0.8 cm. Diameter: About 1.0 mm. Texture: Upper surface: Glabrous with very delicate short feathers like hairs; Under surface: Glabrous with very delicate short feathers like hairs. Color: Green, RHS 137B.

Flowering:

*Blooming period*.—All year round in a moderate climate or in a greenhouse environment. In Israel, flowering occurs between February and November outdoors.

*Flowering response time*.—About 6 weeks from planting of unrooted cutting.

*Flowering longevity*.—On the plant: about 3 to 5 days, depending on temperature; flowers persistent.

Inflorescence:

*Arrangement and type*.—Bilabiate flowers arranged in verticillasters on spikes.

*Orientation at opening*.—Facing outward.

*Quantity*.—Per Plant with at least one open flower: About 10 (spikes) at 8 weeks. Per Verticillaster with fully open flowers: About 6.

*Inflorescence size*.—Height: About 10 cm to 15 cm. Diameter: About 5 cm.

*Flower size*.—Length: Upper lip: about 0.5 cm; Lower lip: about 0.8 cm. Depth: Upper lip: about 0.3 cm; lower lip: about 1 cm.

*Fragrance*.—Very sweet, nectar-like fragrance.

Bud:

*Rate of opening*.—About 1 to 2 days, according to weather.

*Shape*.—Ovoid.

*Length*.—About 6 mm.

*Diameter*.—About 3 mm.

*Color*.—Apex: Green-white, RHS 157B. Base: Green-white, RHS 157B.

*Texture* (*both surfaces*).—Lightly pubescent with very delicate short feathers like hairs.

Petals:

*Quantity*.—Two.

*Arrangement*.—One upper lip and one lower lip with 3 lobes. Lips are fused at base. Upper lip has smooth short feather like hairs, lower lip is smooth and hairless.

*Upper lip*.—Overall shape: Oblong. Apex shape: Rounded. Base shape: Fused. Length (from throat): About 1.5 cm. Width: About 1.0 cm. Margin: Entire. Texture: Upper surface: Smooth, short feather like hairs; Under surface: Glabrous. Color: When opening: Upper surface (including margin): Green-white, RHS 157B; Under surface (including margin): White, RHS N155A. When fully opened: Upper surface (including margin): Green-white, RHS 157B; Under surface (including margin): White, RHS N155A.

*Lower lip*.—Overall shape: Rounded. Apex shape: Blunt. Base shape: Fused. Length: Lateral lobe: About 0.7 cm; Central lobe: About 1.0 cm. From throat: About 1.6 cm. Width: Lateral lobe: About 0.4 cm; Central lobe: About 0.8 cm. Margin: Entire.

*Texture*.—Upper lip: Upper surface: Smooth, short feather like hairs; Under surface: Glabrous.

*Lower lip*.—Upper surface: Glabrous; Under surface: Glabrous.

*Color*.—When opening: Upper surface (including margin): Green-white, RHS 157B; Under surface (including margin): White, RHS N155A. When fully opened: Upper surface (including margin): Green-white, RHS 157B; Under surface (including margin): White, RHS N155A.

Throat:

*Length*.—About 0.3 cm.

*Width*.—About 0.3 cm.

*Texture*.—Outside: Glabrous; Inside: Glabrous.

*Color*.—Outside: White, RHS N155A. Inside: White, RHS N155A.

Calyx:

*Shape*.—Two sepals fused into a tube.

*Length*.—About 2 mm.

*Diameter*.—About 2 mm.

Sepals:

*Quantity per flower*.—2, fused to form a tube.

*Length*.—About 0.7 cm.

*Width*.—About 0.4 cm.

*Shape*.—Tubular.

*Apex*.—Mucronulate.

*Base*.—Fused.

*Margin*.—Entire.

*Texture*.—Upper: Glabrous, with rough lines; Under: Glabrous.

*Color*.—Upper: Green-white, RHS 157B. Under: Yellow-green, RHS 144A.

Peduncle:

*Length*.—About 4.0 cm.

*Diameter*.—About 0.5 mm.

*Angle*.—About 30° from vertical.

*Strength*.—Strong.

*Texture*.—Glabrous, with smooth, short feather-like hairs.

*Color*.—Closest to grey-green, RHS 189D.

Pedicels:

*Length*.—About 0.5 cm.

*Diameter*.—About 1.0 mm.

*Angle*.—About 30° from peduncle axis.

*Strength*.—Strong.

*Texture*.—Glabrous, with smooth, short feather-like hairs.

*Color*.—Closest to grey-green, RHS 192D.

Reproductive organs:

*Androecium*.—Stamen: Number: 2 per flower. Length: About 5 mm. Color: White, RHS N155A. Anther: Length: About 1.5 mm. Width : About 1.0 mm. Color: White, RHS N155A. Filament: Length: About 3 mm to 4 mm. Color: White, RHS N155A. Pollen: Amount: Sparce. Color: Closest to yellow-orange, RHS 165A.

*Gynoecium*.—Pistil: Number: One per flower. Length: About 1.0 mm. Stigma: Length: About 3 mm. Width: About 0.5 mm. Color: White, RHS N155A. Style: Length: About 8 mm. Color: White, RHS N155A. Ovary: Length: About 12 mm. Width: About 1.0 mm. Color: White, RHS N155A.

Seed:

*Quantity*.—About 4.

*Length*.—About 2.5 mm.

*Width*.—About 1.5 mm.

*Shape*.—Ovoid.

*Texture*.—Smooth.

*Color*.—Greyed-orange, RHS 164B.

Fruit: Nutlet, Grey-brown, RHS N199B. Diameter approximately 0.5 cm.

Disease/pest resistance: No information is currently available.

Disease/pest susceptibility: Typically not affected by pests, occasionally thrips. Damping-off in seed beds, downy and powdery mildews and botrytis.

What is claimed is:

1. A new and distinct *Salvia farinacea* plant named 'DANSALFN13', as illustrated and described herein.

* * * * *